(12) United States Patent
Inada et al.

(10) Patent No.: US 7,745,689 B2
(45) Date of Patent: Jun. 29, 2010

(54) NEPHROPATHY-ASSOCIATED GENE

(75) Inventors: Akari Inada, c/o Department of Metabolism and Clinical Nutrition, Kyoto University Hospital, 54, Shogoin Kawara-cho, Sakyo-ku, Kyoto-shi, Kyoto 6068507 (JP); Atsushi Fukatsu, Kyoto (JP); Yutaka Seino, Kyoto (JP)

(73) Assignee: Akari Inada, Fukuoka (JP)

( * ) Notice: Subject to any disclaimer, the term of this patent is extended or adjusted under 35 U.S.C. 154(b) by 0 days.

(21) Appl. No.: 10/545,276

(22) PCT Filed: Feb. 13, 2004

(86) PCT No.: PCT/JP2004/001583

§ 371 (c)(1),
(2), (4) Date: Aug. 11, 2005

(87) PCT Pub. No.: WO2004/072282

PCT Pub. Date: Aug. 26, 2004

(65) Prior Publication Data

US 2006/0140945 A1 Jun. 29, 2006

(30) Foreign Application Priority Data

Feb. 14, 2003 (JP) .............................. 2003-036340

(51) Int. Cl.
*A01K 67/00* (2006.01)
*G01N 33/15* (2006.01)
(52) U.S. Cl. ............................................ 800/18; 800/3
(58) Field of Classification Search .................... 800/3, 800/18
See application file for complete search history.

(56) References Cited

FOREIGN PATENT DOCUMENTS

JP 4-248941 9/1992

OTHER PUBLICATIONS

Hay and Docherty, Diabetes 55(12): 3201-3213, 2006.*
Inada et al 1999, of record in IDS.*
Kuroiwa et al, Nature Genetics 36(7):775-80, 2004; Epub Jun. 6, 2004.*
Moreadith et al, J. Mol. Med. 75(3): 208-216, 1997.*
Polejaeva et al, Theriogenology, 53(1):117-126, 2000.*
Rulicke et al, Experimental Physiology 85: 589-601, 2000.*
Bishop, Reprod. Nutr. Dev. 36: 607-618, 1998.*
Mullins et al, Journal of Clinical Investigation 97(7): 1557-1560, 1996.*
Houdebine, J. Biotech. 34: 269-287, 1994.*
Pearson, Nature 415(6867):8-9, 2002.*
Wall, Theriogenology 45: 57-68, 1996.*
Mullins et al, Hypertension 22: 630-633, 1993.*
Denning, Nat. Biotech. 19:559-562, 2001.*
Humpherys et al, Science 293:95-97, 2001.*
Wall et al, J Dairy Sci. 80:2213-2224, 1997.*
Yanagimachi, Mol. Cell Endocrinol. 187:241-248, 2002.*
Kappell et al, Current Opinion in Biotechnology 3: 549-553, 1992.*
Cameron, Molec. Biotech. 7: 253-265, 1997.*
Sigmund, Arterioscler. Throm. Vasc. Biol. 20: 1425-1429, 2000.*
Anders and Schlondorff, Exp. Nephrol. 8: 181-193, 2000.*
Foulkes et al, 1991, of record in IDS.*
Walker et al, PNAS 91:12423,12427, 1994.*
Lalli et al, Philosophical Transactions: Biological Sciences 3351(1336), Current Understanding of Signaling Pathways, pp. 201-209, 1996.*
Bodor et al , J. Leukocyte Biology 69: 1053-1059, 2001.*
Harada et al, Neuroscience Research 31 (Suppl. 1): S219, Abstract 453, 1998.*
Yamamoto et al, 2001, of record in IDS.*
Jhala et al, Genes and Development 17: 1575-1580, 2003; available online Jul. 1, 2003.*
Inada et al, Molecular and Cellular Biology 24(7): 2831-2841, 2004.*
Taketomi and Ikeda, "KK and KKAy Mice", pp. 129-142, "Animal Models of Diabetes, A Primer" in Frontiers in Animal Diabetes Research, edited by Sima and Shafrir, Harwood Academic Publishers, 2001.*
Odaka et al, "Characteristics of Wistar Fatty Rat", pp. 159-170, ibid.*
Seq Id No:1 search result, example only.*
Shockett et al, PNAS 92: 6522-6526, 1995.*
Inada et al, Biosci. Biotechnol. Biochem. 71(8):1920-1926, 2007.*
Hotta et al, J. Exp. Med. 188(8):1445-1451, 1998.*
Sugimoto et al, Diabetes Metab. Res. Rev. 16(5):354-363, 2000.*
Radu, Roum. Arch. Microbiol. Immunol. 60(3):203-226, 2001; Abstract only.*
Wall et al, Cloning and Stem Cells 3(4):209-220, 2001.*
Foulkes, N. S. et al. (1991) "CREM gene: use of alternative DNA-binding domains generates multiple antagonists of camp-induced transcription" *Cell* 64:739-749.
Goding, J.W. (1980) "Antibody production by hybridomas" *J. Imm. Meth.* 39:285-308.
Hochkeppel, H-K. et al. (1981) "Monoclonal antibodies against human fibroblast interferon" *Eur. J. Biochem.* 118:437-442.
Hussain, M.A. (2000) "Glucagon stimulates expression of the inducible cAMP early repressor and suppresses insulin gene expression in pancreatic β-cells" *Diabetes* 49:1681-1690.
Inada, A et al. (1999) "The cyclic AMP response element modulator family regulates the insulin gene transcription by interacting with transcription factor IID" *J. Bio. Chem.* 274:21095-21103.

(Continued)

*Primary Examiner*—Kevin K. Hill
(74) *Attorney, Agent, or Firm*—Wenderoth, Lind & Ponack, L.L.P.

(57) ABSTRACT

A nephropathy-associated gene which encodes a transcription repressor; and a nonhuman transgenic animal suffering from nephropathy which is constructed by transferring the above gene and allows the observation of increases in urinary volume, urinary albumin and urinary NAG, pyelectasis, enlargement in kidney tubule and glomerular swelling at the early stage and the following sclerosis.

4 Claims, 12 Drawing Sheets

OTHER PUBLICATIONS

Inada, A. et al. (1998) "Transcriptional repressors are increased in pancreatic islets of type 2 diabetic rats" *Biochem. Biophys. Res. Comm.* 253:712-718.

Inada, A. et al. (2001) "A new diabetic model: study in mice overexpressing ICER in pancreatic Beta cells" Abstract 45-0R, *Abstracts from the ADA 61st Scienctific Sessions*.

Inada, A. et al. (1999) "Tensya Inshi CREM ni yoru HIto INsuline Idenshi no Tensya Tyousetu Koko" Bunshi Tonyobyogaku [*Molecular Diabetology*]10:73-81, with English Abstract.

Kohler, G. et al. (1975) "Continuous cultures of fused cells secreting antibody of predefined specificity" *Nature*, 256:495-497.

Secher, D.S. et al. (1980) "A monoclonal antibody for large-scale purification of human leukocyte interferon" *Nature*, 285:446-450.

Stehle, J.H. et al. (1993) "Adrenergic signals direct rhythmic expression of transcriptional repressor CREM in the pineal gland" *Nature*, 365:314-320.

Takamura, E et al. (1998) "Transgenic mice overexpressing type 2 nitric-oxide synthase in pancreatic β cells develop Insulin-dependent diabetes without insulitis" *J. Bio. Chem.* 273:2493-2496.

Yamamoto, Y. et al. (2001)"Development and prevention of advanced diabetic nephropathy in RAGE-overexpressing mice" *J. Clin. Invest.* 108:261-268.

International Search Report from PCT priority application No. PCT/JP2004/0015383.

Accili, D. et al. 1996 "Early neonatal death in mice homozygous for a null allele of the human insulin receptor gene" *Nature Genetics* 12:106-109.

Akari, I. et al. 2005 "Induced ICER Iγ down-regulates cyclin A expression and cell proliferation in insulin-producing β cells" *Biochem and Biophys Res Comm* 329:925-929.

* cited by examiner

A

WT

Tg

B

SEQUENCE LISTING

<160> NUMBER OF SEQ ID NOS: 9

<210> SEQ ID NO 1
<211> LENGTH: 436
<212> TYPE: DNA
<213> ORGANISM: rattus

```
<400> SEQUENCE: 1
actttatttt ggactgtggt acggccaaca agaccactct gtatgcaaaa gcccaacatg    60
gctgtaactg gagatgaaac tgatgaggag actgaccttg ccccaagtca catggctgct   120
gccacaggtg acatgccaac ttaccagatc cgagctccta ctactgcttt gccacaaggt   180
gtggtgatgg ctgcctcacc aggaagcctg cacagtcccc agcaactagc agaagaagca   240
actcgcaagc gggagctgag gctgatgaaa acagggaag ctgctaaaga atgtcgacgt    300
cgaaagaaag agtatgtcaa gtgtcttgag agtcgagtcg cagtgctgga agttcagaac   360
aagaagctta tagaggagct tgaaactttg aaagacattt gctctcccaa aacagattag   420
tagaaatatt taacta                                                  436

<210> SEQ ID NO 2
<211> LENGTH: 2345
<212> TYPE: DNA
<213> ORGANISM: Mus musculus

<400> SEQUENCE: 2
aaaaagtata tgaggacaaa tgtaaggcaa atgaccatgg aaacagttga atcacagcag    60
gatcgaagtg taacacgttc tgtggcagag catagctctg ctcatatgca gactggtcaa   120
atttctgttc ctactctagc tcaggtagca acaattgcag agacagatga ttctgcagac   180
tcagaagtaa ttgattcgca taaacgtaga gaaattcttt cacgaagacc ctcatataga   240
aaaatactga tgaactttc ctctgatgtg cctggtattc ccaagattga agaagaaaaa    300
tcagaggaag aagggacacc acctaacatt gctaccatgg cagtaccaac tagcatatat   360
cagactagca cggggcaata caatgaggag actgaccttg ccccaagtca catggctgct   420
gccacaggtg acatgccaac ttaccagatc cgagctccta ctactgcttt gccacaaggt   480
gtggtgatgg ctgcctcacc aggaagcctg cacagtcccc agcaactagc agaagaagca   540
actcgcaagc gggagctgag gctgatgaaa acagggaag ctgcccggga gtgtcgcagg    600
aagaagaaag aatatgtcaa atgtcttgaa atcgtgtgg ctgtgcttga aaatcaaaac    660
aagaccctca ttgaggaact caaggccctc aaagaccttt attgccataa agcagagtaa   720
ctgtgtttga tttggacctt gttgactgtg aactctaatc ggggcaggcg atgcagcatc   780
ctcataatgg ccatgtggac ttgtagatgg gtctcttaac ccttgcttaa gaatacagtc   840
tgctgtagag tgtgaattgg gaatactgtt ccatggggttg gaatgcagct cccctcacat   900
taccaagctt gctctattgc caatagcatg caacatatgt tttgtttgcc cttctgcttc   960 tactttttc agggaagctg ctaaagaatg tcgacgtcga agaaagagt atgtgaagtg   1020 tcttgagagt cgagtcgcag tgctggaagt tcagaacaag aagcttatag aggagcttga   1080
aactttgaaa gacatttgct ctcccaaaac agattagtag aaatatttaa ctatgaactg   1140
attacagcat gtacagttgc ttttgaatgc aatacaaata tatagccggc aagaattatg   1200 gcttttcct ttgtatcatt catctaactt tctaaaacta acattcctaa gatgctttgt    1260
tgtatttaat ttgctcttac ctctaaggtc aattttttag aagagacaaa ctcaaaaaat   1320
gtatgtaaca aattcttaaa atgaagtatt tgtaagactt gttccagtca acatatttac   1380
agttcccagt ctctctgtca tgaatagtgt cctatgcaat aaaaattttg caggttttaa   1440
gaatcatttt aggaaagggt gaatcaaagg cagtgcatct ctccagtagt aagataaaat   1500
caacccatag agatacctca ggaaagaatg aaaggaagtg tatcctgatg acatgacgtg   1560
agaatagcct acaaatgaat ttatgcattt atagattttt ataatcgtca ctttgtaaag   1620
```

-continued

```
aaagtattgt attgctgtcc ttgggtgcca cagttgaaga cagttttaaa tagaaccatg    1680
ttggttgctc tttgtactat ttggtattta tttaagtatc tgagcattta ctacagcttc    1740
ctactatgta tgtagtatgt gaatttctac aaaagtttgt gctctttgct gttatttaat    1800
gaaagagaca acatattttc attatctgga atgagttcca caagtatgaa tttattgcta    1860
cactggatca gcagccttgc aaatactggg ccatttcatt agaggacaac agcagggctc    1920
taggagcaga gttcagtgtg gagcacttgc ctggcatgct acatgttcag ttgaaaggga    1980
agacctcaag ctctgcaaat ggaatggggt ccaggggaag aggttagagg ttagcctttg    2040
tgctgtacta ggcttcttgc tgatcgtctg gagagtttct gctgatgacc ctccattgtg    2100
aattcttgca acctcaggaa tgttaacgtt taaaaaactt cccaagatgt cattttttgat   2160 tttacaactt ggatcaattt tgttttgctc tttggaatat agctgtgtac atttgtcacg    2220
taggtttagg ctggccttaa actcacagtt ctcttgcctc agccttctga gtgcttggat    2280
tacggatgtg ggccagaata ccagtttga tcaagtattc ttttataaaa tattactttc     2340
ttttt                                                                2345
```

```
<210> SEQ ID NO 3
<211> LENGTH: 25
<212> TYPE: DNA
<213> ORGANISM: mouse

<400> SEQUENCE: 3
atgggctctg agactataaa gccag                                          25

<210> SEQ ID NO 4
<211> LENGTH: 20
<212> TYPE: DNA
<213> ORGANISM: mouse

<400> SEQUENCE: 4
tggatcctga gaacttcagg                                                20

<210> SEQ ID NO 5
<211> LENGTH: 20
<212> TYPE: DNA
<213> ORGANISM: mouse

<400> SEQUENCE: 5
gctggttatt gtgctgtctc                                                20

<210> SEQ ID NO 6
<211> LENGTH: 25
<212> TYPE: DNA
<213> ORGANISM: mouse

<400> SEQUENCE: 6
cagtttcatc tccagttaca gccat                                          25

<210> SEQ ID NO 7
<211> LENGTH: 19
<212> TYPE: DNA
<213> ORGANISM: mouse

<400> SEQUENCE: 7
ctgctttatg gcaataagg                                                 19

<210> SEQ ID NO 8
```

-continued

```
<211> LENGTH: 20
<212> TYPE: DNA
<213> ORGANISM: mouse

<400> SEQUENCE: 8
atccgtaaag acctctatgc                                        20

<210> SEQ ID NO 9
<211> LENGTH: 20
<212> TYPE: DNA
<213> ORGANISM: mouse

<400> SEQUENCE: 9
aacgcagctc agtaacagtc                                        20
```

NEPHROPATHY-ASSOCIATED GENE

This application is the U.S. National Phase under 35 U.S.C. §371 of International Application PCT/JP2004/001583, filed Feb. 13, 2004, which claims priority to Japanese Patent Application No. 2003-36340, filed Feb. 14, 2003. The International Application was published under PCT Article 21(2) in a language other than English.

TECHNICAL FIELD

The present invention relates to a nephropathy-associated gene, a transgenic non-human mammalian animal constructed by transferring the gene, a therapeutic agent for nephropathy, and a method for screening medicines effective for diagnosis or treatment of the nephropathy. The invention relates particularly to diabetic nephropathy in the nephropathy.

BACKGROUND ART

Nephropathy, for which no specific medicine is available, requires an artificial dialysis treatment in an advanced stage even though this treatment inflicts pain on patients. In particular, diabetic neuropathy has become a serious problem as the number of patients with diabetes has increased.

With regards to mechanisms of onset of diabetes, it is well known that severe insulin dysfunction induces a diabetic condition. Recently, one of the mechanisms for insulin dysfunction has been elucidated (Inada A. et al., Bunshi Tonyobyogaku [Molecular Diabetology] 10:73-81, 1999), and elucidation of the onset mechanism of and studies on the treatment of diabetes have been actively performed. However, for mechanisms of onset diabetic complications involving diabetic nephropathy, diabetic retinopathy and diabetic mental disorder, there is no effective and established diagnostic or therapeutic management.

Meanwhile, to develop diagnostic or therapeutic management of diabetes or diabetic complications, vigorous effort has made to establish optimal animal models. (JP 04-248941 A). However, animal model so far exhibits only hyperglycemia with low insulin but not diabetic complications identical to that of human. It has been reported that only a double transgenic (Tg) mouse obtained by crossing two gene-modified Tg mice exhibits diabetic nephropathy (J. Clinical Investigation, Vol. 108, No. 2, p. 261, 2001). However, in this double Tg mouse model, to develop diabetes and to maintain hyperglycemia, it is required to cross a Tg mouse that specifically overexpress inducible Nitric Oxide (iNOS) in insulin-producing β cells (J. Biol. Chem., Vol. 273, pp.2493-2496, 1998) with a Tg mouse overexpressing receptor for advanced glycosylation endproduct (RAGE) in vascular cells. High proteinuria and glomerulosclerosis which are similar to human diabetic nephropathy appear only when both transgenes are simultaneously expressed. In addition, modified overexpressions of iNOS in pancreatic β cells and RAGE in vascular cells are unusual situation. Thus, this model is artificial and far from actual diabetic condition, and no single animal model develops renal changes identical to those seen in humans.

It has been known that ICER suppresses insulin (A. Inada et al JBC 1999 vol. 274 no. 30 p. 21095-21103; A. Inada et al BBRC 1998 vol. 253 no. 3 p. 712-718) gene transcription, and that ICER is increased in the diabetic condition (Inada A. et al BBRC 1998 vol. 253 no. 3 p. 712-718), but no association of ICER with diabetic nephropathy has been known.

Thus, the development of a medicine effective for the diagnosis or the treatment of nephropathy including diabetic nephropathy and the development of a useful experimental system as a pathogenic model of nephropathy or diabetic nephropathy have been highly required.

The present invention mainly intends to provide a method useful for the diagnosis and the treatment of nephropathy including diabetic nephropathy and a transgenic non-human mammalian animal useful as a pathogenic model of diabetic nephropathy.

DISCLOSURE OF INVENTION

The present inventor carried out extensive studies mainly aiming at solving the above subject matters. As a result of making a transgenic mouse (ICER Iγ Tg mouse) in which both insulin synthesis and β-cell proliferation are inhibited and after performing extensive studies, the present inventor has found that the ICER Tg mouse develops diabetes that stably expresses major clinical and pathological features of human diabetic nephropathy, and has completed the present invention by further analyses.

That is, the present invention relates to the followings.

[1] A nephropathy-associated gene characterized by encoding an insulin transcription repressor belonging to a transcription factor CREM family.

[2] The gene according to [1] wherein the insulin transcription repressor is any one selected from the group consisting of CREMα, ICER I and ICER Iγ.

[3] The gene according to [1] wherein the insulin transcription repressor is ICER Iγ.

[4] The gene according to [1] having a base sequence represented by SEQ ID NO:1, a complementary sequence thereof or a nucleotide sequence which hybridizes therewith under a stringent condition, and capable of developing nephropathy.

[5] The gene according to [1] having a base sequence represented by SEQ ID NO:2, a complementary sequence thereof or a nucleotide sequence which hybridizes therewith under a stringent condition, and capable of developing nephropathy.

[6] The gene according to [1] wherein the nephropathy is diabetic nephropathy.

[7] The gene according to [1] wherein the above gene is derived from human.

[8] A nephropathy developing agent comprising the gene according to any one of [1] to [7].

[9] A diabetic nephropathy developing agent comprising the gene according to any one of [1] to [7].

[10] A probe for determination or diagnosis of human nephropathy composed of 15 base or more nucleotide sequence capable of hybridizing with the gene according to [7] under a stringent condition.

[11] A nephropathy-associated protein having an activity of an insulin transcription repressor belonging to a transcription factor CREM family.

[12] The nephropathy-associated protein according to [11] which is any one selected from the group consisting of CREMα, ICER I and ICER Iγ.

[13] The protein according to [11] derived from human.

[14] An antibody which specifically binds to the protein according to any of [11] to [13] or a part thereof.

[15] The antibody according to [14] which specifically binds to a human nephropathy-associated protein.

[16] A diagnostic medicine of human nephropathy containing the antibody according to [15].

[17] An antisense DNA for the human nephropathy-associated gene according to [7].

[18] A preventive or therapeutic agent of neuropathy containing the antibody according to [15] or the antisense DNA according to [17] as an active component.

[19] A method for determining or diagnosing nephropathy having a step of examining an expression level of the human nephropathy-associated gene according to [7] in a specimen using the probe according to [10] or the antibody according to [12].

[20] A transgenic non-human mammalian animal introducing the gene according to any one of [1] to [6].

[21] The mammalian animal according to [20] that develops nephropathy.

[22] The mammalian animal according to [21] wherein the nephropathy is diabetic nephropathy.

[23] The mammalian animal according to [20] that develops diabetes.

[24] The mammalian animal according to [23] wherein the diabetes combines with diabetic nephropathy.

[25] A method for making a transgenic non-human mammalian animal having a step of introducing the gene according to any one of [1] to [6].

[26] A method for screening a preventive or therapeutic agent for at least one selected from the group consisting of nephropathy, diabetic nephropathy and diabetes, having a step of administering a subject substance to the transgenic non-human mammalian animal according to any one of [20] to [25] and measuring an effect of the subject substance on at least one selected from the group consisting of nephropathy, diabetic nephropathy and diabetes of the mammalian animal.

[27] An expression vector capable of stably expressing in mammalian cells, incorporating a marker gene under the control of a promoter of the human nephropathy-associated gene according to [7].

[28] A mammalian cell transformed with the expression vector according to [27].

[29] The cell according to [28] wherein the mammalian cell is a human cell.

[30] A method for screening a preventive or therapeutic agent for at least one selected from the group consisting of human nephropathy, diabetic nephropathy and diabetes, comprising a step of culturing the mammalian cells according to [28] or [29] in the presence of a medicine candidate compound and a step of culture of the mammalian cells and a step of measuring an amount of the expressed marker gene in the presence or absence of the candidate compound.

[31] A preventive or therapeutic agent for at least one selected from the group consisting of human nephropathy, diabetic nephropathy and diabetes, containing a substance obtained by the method for screening according to [26] or [30] as an active component.

BRIEF DESCRIPTION OF DRAWINGS

FIG. 1a shows a produced construct. FIG. 1b shows a detection result of ICER Iγ mRNA. The ICER Iγ mRNA was correctly expressed from the transgene construct in ICER Iγ Tg mice. FIG. 1c shows protein expression of ICER Iγ detected by Western blotting. The protein, at a large amount, was expressed in ICER Iγ Tg mice. FIG. 1d shows insulin mRNA amounts. The insulin mRNA was scarcely expressed in ICER Iγ Tg mice.

FIG. 2a shows the changes of the blood glucose levels, and white and black circles indicate wild type (WT) and ICER Iγ Tg mice, respectively. FIG. 2a shows the changes on day 0 and day 7. The blood glucose level was increased in ICER Iγ Tg mice on the 7th day after birth. FIG. 2b shows the changes of the blood glucose levels for 20 weeks. Tg mice develop severe diabetes as early as 2 weeks of age and sustain hyperglycemia. FIG. 2c shows the changes of plasma insulin levels. Insulin synthesis was suppressed in ICER Iγ Tg mice. FIG. 2d shows the changes of ketone bodies (acetone, acetoacetic acid and β-hydroxybutyric acid). The levels of the ketone bodies were increased in ICER Iγ Tg mice. FIG. 2e shows the changes of glucagon levels. Production of glucagon was increased in ICER Iγ Tg mice.

FIG. 3b shows the changes on 0 day and the 7th day after birth. FIG. 3a is a photograph of a male Tg mouse and control littermate (WT) at 12 weeks of age. FIG. 3c show the growth curve of male mice from day 0 to 20 weeks of age. There was no difference in growth until 7 days after birth (FIG. 3b), but the growth of ICER Iγ Tg mice was suppressed around 6 weeks of age (FIG. 3c).

C: Dual staining of glucagon (green) and IAPP (red) as a β-cell marker was analyzed by confocal microscopy. In ICER Iγ Tg mice, β cells were reduced in number and most of the islet was glucagons positive. A few cells co-expressing IAPP and glucagons were present. Because the insulin level is significantly decreased and anti-insulin antibody cannot detect the P cell in ICER Iγ Tg mice, IAPP was used as a β-cell marker to demonstrate the presence of degranulated β cells.

D: Scattered singlets-doublets of insulin-positive cells in ICER Iγ Tg mice at 7 days of age, suggesting that neogenesis of β cells was normally occurred (×400). Thus, in this Tg model, diabetes resulted from a decreased number of β cells, further compounded by impaired insulin expression in individual β cells.

Figure 11:
Figure 11:
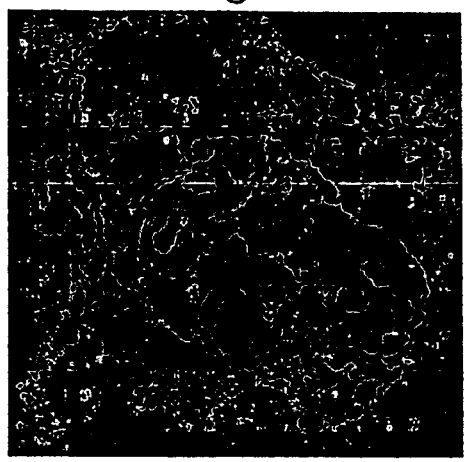
Figure 11:
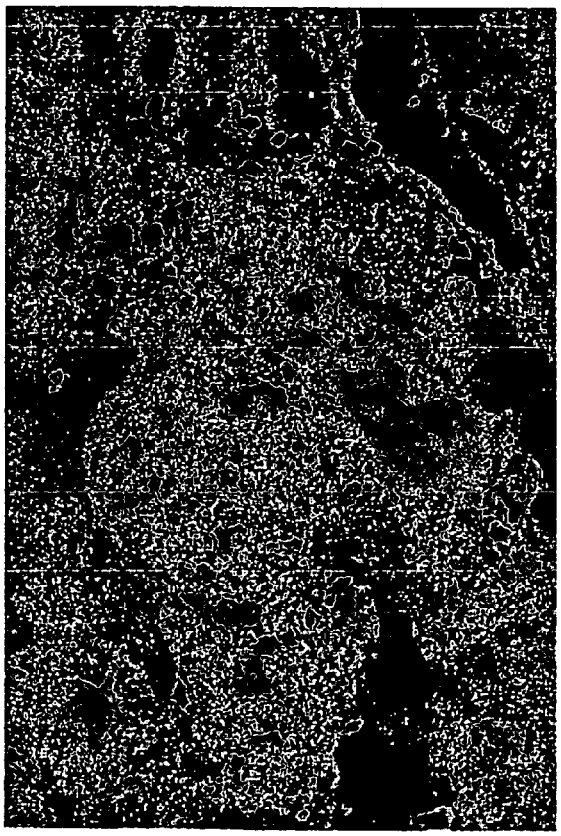
Figure 11:
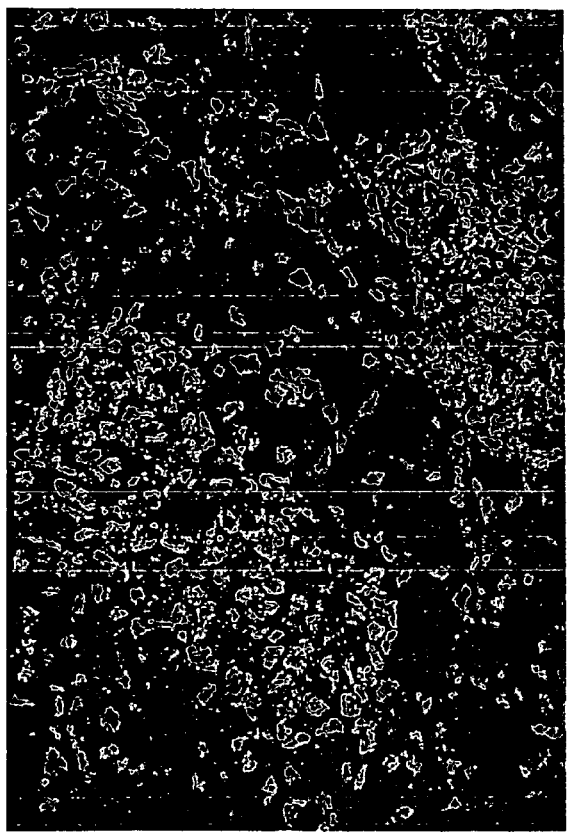

FIG. 11 shows cyclin A expression and proliferation in islets at day 7 of age (line Tg23). A: Dual staining of insulin (red) and Ki67 (green) as a marker of cell proliferation was analyzed by confocal microscopy. Ki67 protein was detected in many nuclei of insulin-positive cells in WT mice but in no insulin-positive cells in ICER Iγ Tg mouse. B: cyclin A expression in islets at day 7 of age. At day 7, normally a time of active cell proliferation, cyclin A protein was detected in most of the nuclei in islets in WT mice but in only a few islets of ICER Iγ Tg mice.

BEST MODES FOR CARRYING OUT THE INVENTION

The present invention is described in more detail below.

Nephropathy-Associated Gene

The gene, according to the present invention, encodes an insulin transcription repressor belonging to the CREM (cAMP responsive element modulator) family which modulates transcription of an insulin gene by binding to a regulatory transcription factor (cAMP responsible element [CRE]). The present inventor has elucidated that the gene is involved in the onset mechanism and pathological progress of nephropathy.

The repressors of insulin gene transcription, belonging to the transcription factor CREM family, include ICER I (inducible cAMP early repressor I), ICER Iγ, CREMα and the like. Among them, ICER Iγ is particularly useful.

The nephropathy-associated gene of the present invention widely encompasses nephropathy-associated genes derived from mammalian animals such as human, rat, monkey, dog, rabbit, hamster, cattle and horse in addition to genes derived from a mouse (SEQ ID NOS:1, 2, etc.), and also encompasses these genes or complementary chains thereof or polynucleotides capable of hybridizing therewith under a stringent condition. In particular, the gene derived from the mouse is useful for the production of transgenic mice, and the gene derived from the human is useful for diagnosis of human nephropathy, evaluation of potential nephropathy in future and search of therapeutic agents for human patients with renal diseases.

Herein, the stringent condition refers to the condition where only specific hybridization occurs and non-specific hybridization does not occur. Such a condition is typically a state of about "1×SSC, 0.1% SDS at 37° C.", preferably about "0.5×SSC, 0.1% SDS at 42° C.", and more preferably about "0.2×SSC, 0.1% SDS at 65° C.". For example, in the case of nephropathy-associated gene derived from the mouse, a DNA obtained by the hybridization usually has high homology to a DNA represented by a base sequence described in SEQ ID NO: 1 or 2. The high homology indicates a homology of 60% or more, preferably a homology of 75% or more, and most preferably a homology of 90% or more. Furthermore, the DNA obtained by the hybridization or a nephropathy-associated protein encoded by the gene has an effect to develop nephropathy.

The transcription repressor which belongs to the CREM family is a regulatory factor of insulin and cyclin A gene transcription activity. When this repressor is excessively expressed, the insulin production is reduced, and β-cell replication are inhibited. As a result, islets have reduced β-cell numbers and impaired insulin secretion, leading to chronic hyperglycemia, which results in severe diabetes. The present inventor has elucidated that ICER Tg mouse model exhibits not only severe diabetes but also develops progressive diabetic nephropathy. These results suggest that the repressor and the gene encoding repressor are deeply involved in onset and pathological progress of nephropathy.

The nephropathy-associated genes of the present invention having such properties contribute to elucidate an onset mechanism and progress of nephropathy, to further elucidate pathogenesis and treatment of patients with nephropathy, and can be used usefully for nephropathy onset, analysis of nephropathy, detection of nephropathy, diagnosis of nephropathy and the like.

In particular, when the gene of the invention is highly expressed, diabetic nephropathy develops. Thus, it is possible to usefully apply for the onset, analysis, detection and diagnosis of diabetic nephropathy.

The gene of the present invention can be utilized as a nephropathy developing agent or a diabetic nephropathy developing agent by incorporating as needed in a vector and the like under the control of a promoter which is highly expressed in a mammalian animal that is a host. Nephropathy developing agent or diabetic nephropathy developing agent can be utilized for the production of a model animal for diabetic nephropathy development.

The nephropathy-associated gene of the present invention develops the nephropathy (particularly, diabetic nephropathy), and is likely to simultaneously develop diabetic complications (angiopathy, retinopathy, neuropathy etc.) other than nephropathy when the gene is expressed at high levels. In particular, neuropathy is observed in an STZ (streptozotocin)-induced diabetes model, and thus, it is highly likely that the neuropathy also occurs in the transgenic mice of the present invention.

The neuropathy-associated genes and GeneBank access numbers thereof are exemplified below:
AJ311667, AJ292222 (mouse ICER I);
S67786 (mouse ICER Ir);
AB031423 (rat CREM17X)
S66024 (rat ICER II)
U44836 (human ICER I)
S68271, Z15159, Z15158 (human CREM)
U04835 (rat CREM)
M60285 (mouse CREM)

The neuropathy-associated genes of the present invention are not limited thereto, widely encompass the insulin transcription repressors belonging to the CREM family, and further encompass modified genes capable of hybridizing with such insulin gene transcription repressors under the stringent condition.

The neuropathy-associated gene of the invention can be expressed systemically, but it is preferable to selectively express in organs such as pancreas and kidney, preferably the pancreas, and more preferably Langerhans islet cells in the pancreas. For example, selective expression in the Langerhans islet cells can be accomplished by expressing the nephropathy-associated gene under the control of an insulin promoter. The selective expression in the other site/organ can be accomplished by placing the nephropathy-associated gene of the invention under a promoter of a gene to be selectively expressed in the site/organ.

For example, to induce nephropathy (including diabetic nephropathy) and diabetes models, it is further contemplated that expressing repressors under a β-cell specific promoter, such as Pdx-1, or IAPP, as has been discussed for the insulin promoter, would be useful.

When the nephropathy-associated gene of the invention is expressed at a high level, levels of collagen IV and laminin are increased, and these phenomena indicate glomerular sclerosis. When the glomerular sclerosis occurs, a glomerular filtration rate (GFR) is reduced and renal dysfunction occurs to develop renal failure and finally uremia. Concomitantly with this, intravascular pressure is increased to develop hypertension. Therefore, by expressing the nephropathy-associated gene at a high level, it is possible to produce pathological models for various renal diseases.

Probe

A probe of the present invention is composed of a sequence of 15 base or more capable of hybridizing with the above gene of the invention under the stringent condition, particularly composed of a nucleotide sequence complementary to the gene of the invention or a complementary chain thereof, and can be used usefully for the purpose of examining nephropathy-related issues such as determination or diagnosis of nephropathy. It is also possible to use for the analysis or detection of nephropathy. In particular, the probe of the invention can be suitably used for the determination or diagnosis of diabetic nephropathy.

In one preferable embodiment of the present invention, the probe has a part of the sequence of human nephropathy-associated gene subjected to the diagnosis of the human nephropathy.

The probe of the invention can be also utilized as a disease marker by imparting an appropriate label.

The probe or the disease marker of the invention can be used effectively for the diagnosis or determination of nephropathy or diabetic nephropathy such as examinations of presence or absence of the onset of nephropathy or progression stages of nephropathy or diabetic nephropathy by using for a step of contacting with a specimen sample and measuring the presence or absence of and an amount of a gene bound to the probe or an expression product (mRNA) thereof.

Protein

A protein of the present invention has an activity of the insulin transcription repressor belonging to the transcription factor CREM family, and has a function associated with nephropathy. Specifically, the protein has the functions associated with the onset and progression, and development of the symptom of nephropathy. The protein of the invention particularly has the function associated with diabetic nephropathy in nephropathy.

The insulin transcription repressors include, for example, CREMα, ICER I, ICER Iγ, and the like. Among them, ICER Iγ is particularly useful.

A method for obtaining the protein of the invention is not particularly limited, and for example, the protein can be obtained by the following methods.

An expression vector is constructed by inserting the gene of the invention, e.g., the gene having the sequence described in SEQ ID NO:1 or 2 ligated downstream of an appropriate promoter into the vector. Then the resulting expression vector is introduced into a host to produce a transformant. As the vector, for example, it is possible to use retrovirus type vector, papilloma virus vector, vaccinia virus vector, SV40 type vector, baculovirus vector, and the like. As the host, for example, it is possible to use fungi, bacteria, yeast, insect cells, plant cells, animal cells and the like.

The nephropathy-associated protein of the present invention is obtained by culturing the produced transformants and collecting the protein produced and accumulated in the culture. The produced protein can be isolated and purified by publicly known purification methods such as salting out by inorganic salts, fractionated precipitation by organic solvent, ion-exchange resin column chromatography, affinity column chromatography, gel filtration and immunoprecipitation. The protein can also be formulated by publicly known methods.

It appears that the protein of the invention has strong relevance with mechanisms for the onset and progression of nephropathy, and thus, the protein can be utilized effectively for the diagnosis of nephropathy, the analysis of the onset mechanism of nephropathy, determination of malignancy of nephropathy, and the like.

Antibody

An antibody of the present invention is an antibody which binds specifically to nephropathy-associated protein of the invention or a part thereof, can detect or measure the nephropathy-associated protein, and can be usefully utilized for the detection of nephropathy-associated protein, the diagnosis of nephropathy, the detection or determination of nephropathy, the treatment of nephropathy and the like. The antibody of the invention can be suitably used, in particular, for diabetic nephropathy in nephropathy.

The antibody may be a polyclonal antibody or a monoclonal antibody as long as it can bind specifically to the protein of the invention or a part thereof.

The monoclonal antibody is produced, for example as follows. An individual in which an antibody titer has been detected is selected from non-human mammalian animals, e.g., mice immunized with the protein of the present invention or a partial peptide thereof as an antigen, spleen or lymph nodes are removed 2 to 5 days after the final immunization, and antibody-producing cells contained therein are fused with myeloma cells to prepare hybridomas which produce the monoclonal antibody. The monoclonal antibody can be obtained by culturing the hybridomas to produce the antibody and appropriately isolating/purifying the antibody. Cell fusion can be performed in accordance with known methods, e.g., Kohler and Milstein's method (Nature, 256, 495, 1975) and modified methods thereof (J. Immunol. Method, 39, 285, 1980; Eur. J. Biochem., 118, 437, 1981, Nature, 285, 446, 1980). As a fusion accelerator, polyethylene glycol (PEG) and Sendai virus and the like are used. The monoclonal antibody of the invention may be used for humans by using an appropriate method known publicly.

A polyclonal antibody can be produced, for example as follows. Non-human mammalian animals are immunized with the protein antigen itself or a complex thereof with a carrier protein by the same method as in the production of the monoclonal antibody. The polyclonal antibody can be obtained by collecting an antibody against the protein of the invention from the immunized animal and isolating/purifying the antibody.

By the use of the antibody of the present invention, it is possible to detect and measure nephropathy-associated protein. Also by utilizing the antibody of the invention, it is possible to detect, determine or diagnose nephropathy (including diabetic nephropathy). For example, the onset, severity and prognosis of the nephropathy can be determined or diagnosed by contacting the antibody of the invention with a sample prepared from a specimen, and detecting or measuring an expressed amount or an expressed site of nephropathy-associated protein. In particular, the antibody of the invention can be utilized usefully for detection and treatment of the diabetic nephropathy in nephropathy.

The antibody of the invention can also be appropriately formulated to use as a diagnostic, detecting or determining medicine of nephropathy or a preventive or therapeutic agent of nephropathy. The diagnostic medicine of the nephropathy can also be utilized as a pharmaceutical for detecting or measuring the nephropathy-associated protein. The preventive or therapeutic agent of the nephropathy can also be utilized as a pharmaceutical for inhibiting the expression or the function of the nephropathy-associated protein. The pharmaceutical containing the antibody of the invention can be usefully utilized as the diagnostic medicine of diabetic nephropathy or the preventive or therapeutic agent of diabetic nephropathy.

Preventive or Therapeutic Agent

The nephropathy-associated gene of the present invention can be involved in the development of nephropathy, particularly diabetic nephropathy as the complications of the diabetes. Therefore, a substance which inhibits the expression or the function of the gene is useful as not only the preventive or therapeutic agent of nephropathy but also the preventive or therapeutic agent of diabetic nephropathy and furthermore as the preventive or therapeutic agent of the diabetes.

An inhibitor of the expression or the function of the nephropathy-associated gene, an antisense DNA of the gene and the antibody against the nephropathy-associated protein can be useful as the preventive or therapeutic agent for the nephropathy, diabetic nephropathy and diabetes.

Transgenic Non-Human Mammalian Animal

A transgenic non-human mammalian animal in the present invention refers to a mammalian animal other than human, produced by gene recombination by introducing the gene of the invention. The mammalian animals other than human include mice, rabbits, rats, and the like.

Methods for producing the transgenic non-human mammalian animal include a method (microinjection method) of directly introducing the gene in a pronucleus of an ovum with a micropipette under a phase contrast microscope, a method of using an embryonic stem cell (ES cell), a method of inserting the gene into a retrovirus vector or a adenovirus vector to infect the ovum, and a sperm vector method by introducing the gene into the ovum via a sperm.

In one preferable embodiment of the invention, a transgenic mouse (Tg mouse) of the nephropathy-associated gene (e.g., ICER, ICER Iγ) excessively expresses the gene specifically in β cells in pancreas. As a result, the mouse develops the diabetes attributed to hyperglycemia, which can cause the nephropathy, i.e., the pure diabetic nephropathy.

The transgenic non-human mammalian animal of the invention exhibits the following symptoms characteristic for the nephropathy.
1) A urinary volume, a urinary albumin amount and a urinary NAG amount become large.
2) Hypertrophy of renal pelvis is exhibited.
3) Enlargement of renal tubules is exhibited.
4) Early hypertrophy and fibrosing and subsequent sclerosis of glomerulus are observed.

Furthermore, the transgenic non-human mammalian animal of the invention exhibits the following symptoms characteristic of severe diabetes.
5) Polydipsia
6) Polyuria
7) Low body weight
8) Hyperglycemia
9) Low insulin The most important symptoms in the transgenic non-human mammalian animal model of the present invention are the increase of the urinary albumin amount of 1) and the symptoms of 2) to 4) (the hypertrophy of renal pelvis, the enlargement of renal tubules, and the hypertrophy and fibrosing and subsequent sclerosis of glomerulus). In conventional diabetes models, although the increase of the urinary volume has been observed, no proteinuria has been observed. The proteinuria has been observed only in the double transgenic mouse, but its mechanism is considered to be quite different from the actual condition of the diabetes. In particular, the model which exhibits the symptoms (proteinuria and glomerular sclerosis) of the diabetic nephropathy as the complications of the diabetes has been provided by the present invention for the first time.

Therefore, the transgenic non-human mammalian animal of the invention can be utilized usefully as not only an animal model for nephropathy but also as an animal model for diabetes.

In particular, the transgenic non-human mammalian animal of the invention is useful as the diabetic nephropathy model animal because the animal develops the symptoms similar to those of the human diabetic nephropathy. For example, by the use of the transgenic non-human mammalian animal of the invention, it is possible to perform screening for candidate substances of the diagnostic or therapeutic agent for the nephropathy or the diabetic nephropathy. Also by the use thereof, it is possible to examine an appropriate dosage, a dosing period and potential side effects of the candidate substance.

Screening

By applying the present invention, it is possible to efficiently perform the screening for the candidate substance of the diagnostic or therapeutic agent for the nephropathy or the diabetic nephropathy.

For example, the candidate substances of the diagnostic or therapeutic agent for at least one selected from the group consisting of the nephropathy, the diabetic nephropathy and the diabetes can be screened by administering a subject substance to the above transgenic non-human mammalian animal of the invention and measuring an effect of the subject substance on at least one selected from the group consisting of the nephropathy, the diabetic nephropathy and the diabetes of the mammalian animal.

Substances effective for the treatment of nephropathy, diabetic nephropathy or the diabetes can also be screened using the expression of a reporter gene as an indicator by adding the subject substance in the culture system of a human transformed cell line transformed with a vector comprising the human transcription repressor, a promoter of, for example, ICER Iγ and the reporter gene ligated to be expressed by the promoter.

A therapeutic or diagnostic medicine for the nephropathy or the diabetic nephropathy can be produced by appropriately formulating the substance obtained by these screening methods as an active component or preparing it in combination with an appropriate pharmaceutically acceptable carrier.

EXAMPLES

The present invention will be more specifically described with reference to the following Examples, but the invention is not limited to these Examples.

Example 1

(1) Materials and Procedures

Production of ICER Iγ Transgenic Mouse

An ICER Iγ cDNA was inserted downstream of a human insulin promoter in a transgenic plasmid plns-1. A transgene cassette (plns-ICER Iγ plasmid) was cut out with restriction enzymes, purified and introduced into a fertilized ovum of C57BL/6×C57BL/6 (pure C57BL/6 mouse). A transgenic mouse (Tg) was identified by PCR (polymerase chain reaction) analysis of a tail DNA using the following primers.

```
Human insulin promoter,
                                         SEQ ID NO.1
5'-ATGGGCTCTGAGACTATAAAGCCAG-3' (forward);

Rabbit β globin,
                                         SEQ ID NO.2
5'-TGGATCCTGAGAACTTCAGG-3' (forward 1);

SEQ ID NO.3
5'-GCTGGTTATTGTGCTGTCTC-3' (forward 2);

ICER Iγ,
                                         SEQ ID NO.4
5'-CAGTTTCATCTCCAGTTACAGCCAT-3' (reverse 1);
and SEQ ID NO.5
5'-CTGCTTTATGGCAATAAGG-3' (reverse 2);
```

A copy number of the transgene was examined by Southern blotting method. Littermates (wild type: WT) which were not transgenic mice were used in all experiments. All mice were handled in accordance with Animal Facility Guideline at Kyoto University.

Measurement of Blood Glucose Value, Blood Parameters, Blood Pressure and HbA1c

A blood glucose value was measured in whole blood obtained from a tail by an enzyme-electrode method. The blood was quickly obtained from heart before the isolation of pancreas.

Levels of insulin, ketone and glucagon were measured using the following ELISA kits.
Insulin: MORINAGA Institute of Biological Science;
ketone: Sanwa Kagaku; and
glucagons: Yanaihara Institute Inc.

The blood pressure was measured using a tail cuff method.

The HbA1c value was measured using a DCA 2000 analyzer.

Isolation of Pancreatic Islets, Secretion and Content of Insulin

Pancreatic islets were isolated by a collagenase method. Insulin secreting capacity, insulin content and DNA content were measured using fresh pancreatic islets isolated from Tg (n=5) and WT (n=5) at 12 weeks of age by a batch incubation method, RIA and a fluorometric assay, respectively.

RNA Isolation, Reverse Transcriptase-Polymerase Reaction

Total RNA was extracted from the pancreatic islets freshly isolated from Tg (n=10) and WT (n=10) at 10 weeks of age using a trizol reagent (Gibco BRL). The presence of total islet RNA was identified by electrophoresis. A single strand cDNA was synthesized from the total islet RNA using superscript reverse transcriptase. The expression of an ICER Iγ mRNA expressed by the transgene was examined by a PCR method using the mouse islet cDNA and the following oligonucleotide primers.

```
Rabbit β globin;
5'-TGGATCCTGAGAACTTCAGG-3' (forward; SEQ ID NO.2)
and

ICERIγ;
5'-CTGCTTTATGGCAATAAGG-3', (reverse; SEQ ID NO.5)

Control β-actin;
5'-ATCCGTAAAGACCTCTATGC-3', (forward; SEQ ID NO.6)

5'-AACGCAGCTCAGTAACAGTC-3'. (reverse; SEQ ID NO.7)
```

These primers are designed to stride an intron of the gene in order to distinguish the genomic DNA from the mRNA and confirm whether the DNA is not contaminated at an RNA preparation stage. A Tg genomic DNA containing the intron and a WT islet cDNA having no transgene were used as controls. The PCR was performed under a condition of 40 cycles of 94° C. for 15 seconds, 55° C. for 15 seconds, 72° C. for 30 seconds, and 72° C. for 5 minutes. PCR products were electrophoresed on 2% agarose gel and stained with ethidium bromide.

Western Blotting

Western blotting was performed in order to examine the expression of an ICER protein in the pancreatic islets of Tg. The pancreatic islets isolated from Tg (n=3) and WT (n=3) at 10 weeks of age were homogenized in a cell lysis solution (50 mM Tris-HCl(pH7.4), 150 mM NaCl, 1% TritonX-100, 1% sodium deoxycholate, 0.1% SDS, 22 mM EDTA, 1% Trasilol), cell debris was removed by centrifugation, subsequently supernatants were electrophoresed on 4 to 20% polyacrylamide SDS gel and transferred onto a polyvinylidene difluoride membrane in a transfer buffer (25 mM Tris, 190 mM glycine, 20% methanol). The membrane was blocked with 5% skim milk in phosphate-buffered saline, and incubated with an anti-CREM antibody (diluted to 1:250; Santa Cruz Biotechnology, Inc., Santa Cruz, Calif.) at 37° C. for 2 hours. Subsequently, the membrane was incubated with a second antibody, horseradish peroxidase-linked anti-rabbit IgG (Amersham Pharmacia Biotech) at 37° C. for 30 min. At these steps, the membrane was washed three times with 5% Tween 20/phosphate buffer for 10 minutes. The detection was performed in accordance with ECL protocol (Amersham Pharmacia Biotech).

Northern Blotting

The total islet RNA (20 μg) was denatured in a solution of 1×MOPS (5×MOPS: 0.1 M MOPS, 40 mM sodium acetate, 5 mM EDTA), 6.7% formaldehyde and 50% formamide at 55° C. for 15 minutes, subsequently electrophoresed on 1.2% formaldehyde agarose gel and blotted onto a membrane. After prehybridization at 65° C. for one hour, hybridization with a rat insulin cDNA probe was performed overnight. Both of the prehybridization and the hybridization were performed in a solution of 5×sodium chloride-sodium citrate(SSC), 0.1%sodium dodecyl sulfate at 65° C. The membrane was washed twice with a solution of 0.1×SSC and 0.1% sodium dodecyl sulfate at 65° C. for 30 minutes. Gene Images random prime labeling & detection system (Amersham Pharmacia Biotech) was used for labeling and detection of the probe.

Urinary Volume, Urinary Albumin Amount and Urinary NAG Amount

The mice at 4 to 36 weeks of age produced as the above were individually housed in a metabolic cage, and the urine was accumulated for 24 hours. The mice could eat and drink ad libitum during the accumulation of urine. The amounts of urinary albumin and urinary NAG were measured using Alubuwell kit (Exocell Inc.) and NAG test kit (Shionogi), respectively.

Histological Analyses (I) The kidney halves were fixed with a methyl Carnoy solution, embedded in paraffin, and cut into serial sections (2 μm). Kidney sections were stained with PAS (periodic acid-Schiff) and PASM (periodic acid-methenamine silver), and observed by light microscopy. The remaining kidney halves were snap-frozen in cold acetone in OCT compound, and cryostat sections were used for immunohistochemical staining.

A glomerular area was analyzed using the PAS staining. A sclerosis index was measured by scoring PAS-stained specimens (scores 0 to 3: 0=not stained, 1=one-third or more, 2=one-third to two-thirds, 3=two-thirds or more).

For fluorescent staining, the tissue was immediately embedded in an OCT compound, and frozen in acetone-dry ice. This block was sectioned into 3.5 μm sections using a cryostat. A rabbit polyclonal anti-mouse collagen type I antibody (Calbiochem), a rabbit polyclonal anti-mouse laminin antibody (Sigma), a rabbit polyclonal anti-mouse MMP-2 antibody (NeoMarks), and a rabbit polyclonal anti-mouse collagen type IV antibody (Progen Biotechnik) were used as primary antibodies. A FITC-labeled goat anti-rabbit antibody (Burlingame) was used as a second antibody.

(II) Parts of the removed kidney and pancreas were fixed with a Carnoy solution or 10% formalin, and subsequently embedded with paraffin. The remainings were fixed with acetone, and subsequently embedded with OCT, which were then made into frozen sections (4 μm). Parts of kidney sections (3 μm) were used for PAS staining. Morphological analysis was performed by a blind test method using 6 to 8 kidneys at each week of age. The following primary antibodies were used for immunological staining. Anti-ICER Iγ antibody (1:500; provided by Dr. J. F. Habener, Massachusetts General Hospital, Howard Hughes Medical Institute, MA), anti-insulin antibody (1:500; DAKO, Kyoto, Japan), anti-collagen I antibody (1:50; Calbiochem), anti-collagen IV antibody (1:250; Progen), anti-laminin antibody (1:100; Sigma), and anti-mouse MMP2 antibody (1:100; NeoMarks).

The primary antibody was fluorescently detected by a FITC-labeled second antibody or a Texas red-labeled second antibody (1:200). Also after detection by a biotin-labeled second antibody, a DAB staining was performed. Stained sections were photographed using a confocal microscope (Zeiss LSM 410). The expressions of collagen I, collagen IV and laminin were semi-quantitatively analyzed by the blind test method. The following scores were used for the determination: 0=normal, 1=change of 25% or less in the glomerulus, 2=change of 25 to 50%, 3=change of 50 to 75%, and 4=change of 75% or more.

For electron microscopy, specimens were taken from the kidney of ICER Tg (n=4) and WT (n=4) mice at 40 weeks of age, fixed with 2% glutaraldehyde in 0.05 mol/L phosphate buffer, dehydrated in a graded ethanol series, and embedded in epoxy resin according to routine procedures. Sections were cut with a glass knife on a Reichert-Nissei Ultracuts microtome. Sections were contrasted with uranyl acetate and lead citrate and observed with electron microscope. Thickness of GBM was measured by the orthogonal intercept method.

(2) Data Analysis

The above data were represented as mean ±standard error (SE). Statistical comparison was performed using Student's t-test. A P value less than 0.05 was considered to have a significant difference.

(3) Evaluation

Expression of ICER Iγ in Transgenic Mice

Figure 1:
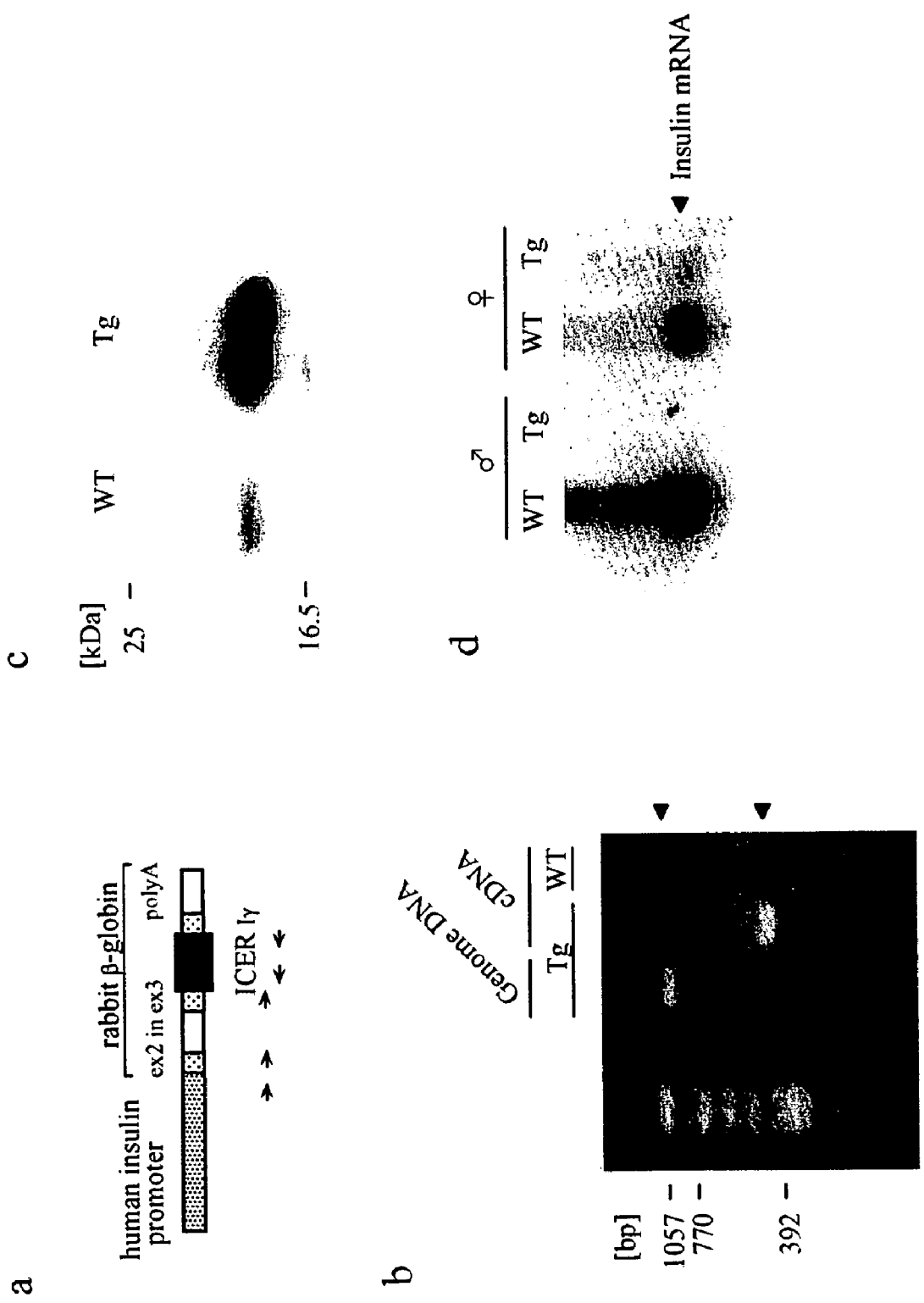
FIG. 1 shows ICER Iγ expression and effects thereof produced in ICER Iγ Tg mice.

Effects of overexpression of ICER Iγ were evaluated using ICER Iγ Tg mice produced by the above method. A construct used is shown in FIG. 1a. The transgenic mice from three lines, i.e., Tg7, Tg12 and Tg23 were used. The presence of ICER mRNA was identified by reverse transcriptase polymerase chain reaction (RT-PCR) by amplifying sequences specific for oligonucleotides specific for rabbit β globin and ICER Iγ. A PCR product in which the intron had been spliced out and which corresponded to ICER Iγ mRNA transcribed from the transgene was detected in ICER Iγ Tg mice (see FIG. 1b). The Tg genomic DNA containing a fragment with intron and the islet cDNA of the WT not containing the fragment were used as the controls. The expression of the ICER Iγ protein was identified by the anti-CREM antibody. It has been already reported that the anti-CREM antibody recognizes the ICER. As a result of performing the Western blotting, it was found that the ICER Iγ was excessively expressed in ICER Iγ Tg mice (see FIG. 1c). Furthermore, the expression levels of insulin mRNA were analyzed using the islet total RNA extracted from ICER Iγ Tg mice and the WT control mice at 10 weeks of age. The expression level of the insulin mRNA was obviously lower in ICER Iγ Tg mice than the control mice (see FIG. 1d).

Down regulation of the insulin mRNA corresponds to the expression of ICER Iγ at a high level, suggesting that the ICER Iγ is involved in the suppression of insulin gene transcription activity.

Moreover, the number of the insulin-producing cells (β cells) has been already reduced on day 0, and the ICER Iγ directly causes the reduction of the β cells (FIG. 10A to D).

It is conceivable that the ICER Iγ excessively expressed in the β cells inhibits the expression of tetracycline A which works importantly at a DNA synthesis phase in a cell cycle to inhibit proliferation of the β cells thereby reducing the number of the β cells in ICER Iγ Tg mice (FIG. 11).

Effects of High Level Expression of ICER Iγ

Figure 2:
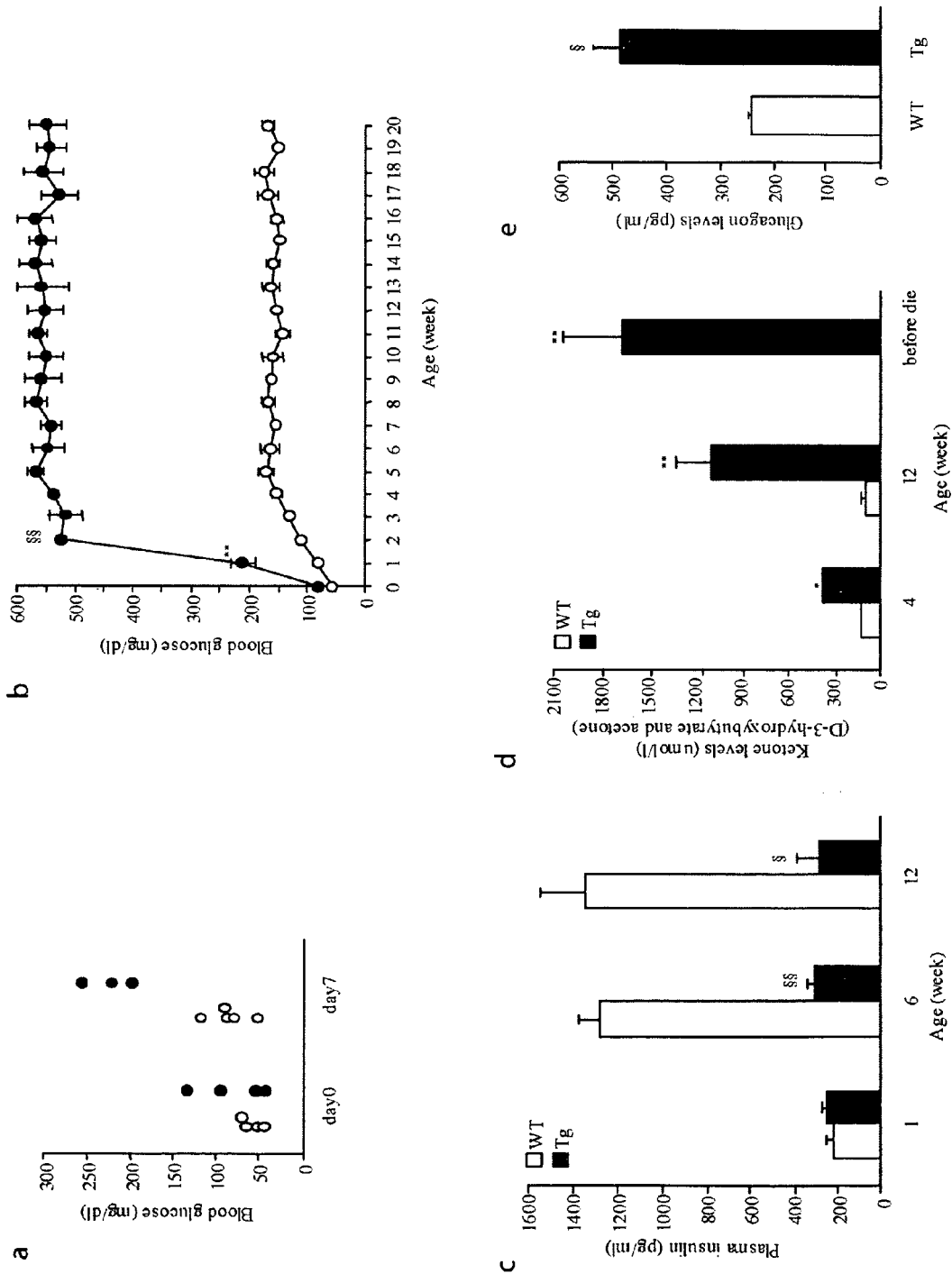
FIG. 2 shows blood glucose levels and variations of blood parameters in order to evaluate the effects of ICER Iγ expression.
Figure 2F:
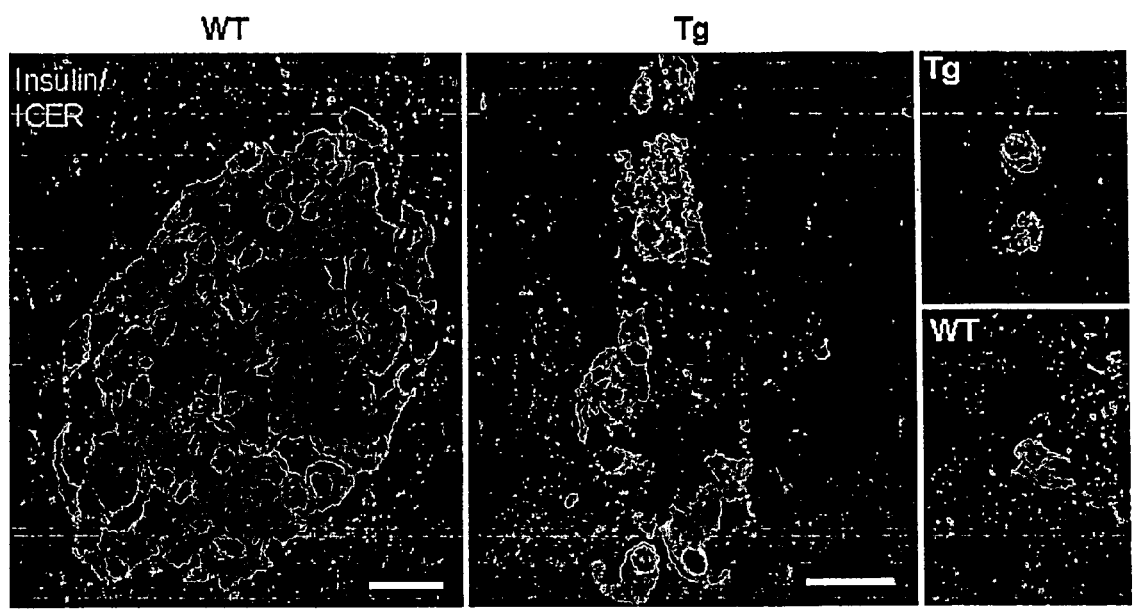
FIG. 2f shows pancreatic islets stained with anti-insulin antibody (green) and anti-ICER Iγ antibody (red) in mice on the 7th day after birth. In ICER Iγ Tg mice, the expression of ICER Iγ and the decrease of insulin-producing cells were observed (a bar represents 10 mm). One or two cells are shown in photographs at the right side.

In order to evaluate the effects of the high level expression of ICER Iγ, blood parameters were measured. ICER Iγ Tg mice developed severe diabetes. Blood glucose levels in ICER Iγ Tg mice were normal on day 0, but increased markedly on day 7, increased further at 2 weeks of age, and remained at these high levels thereafter (see FIGS. 2a and 2b). Insulin concentrations in plasma were remarkably low and only one fifth of the control at 6 weeks of age (see FIG. 2c). Ketone levels in blood were extremely high at 6 and 12 weeks of age, and further increased until time of death (see FIG. 2d). Glucagon levels in plasma were also remarkably high (see FIG. 2e). In ICER Iγ Tg mice, ICER Iγ was expressed, and the number of the insulin-producing cell was reduced (FIG. 2f).

Figure 3:
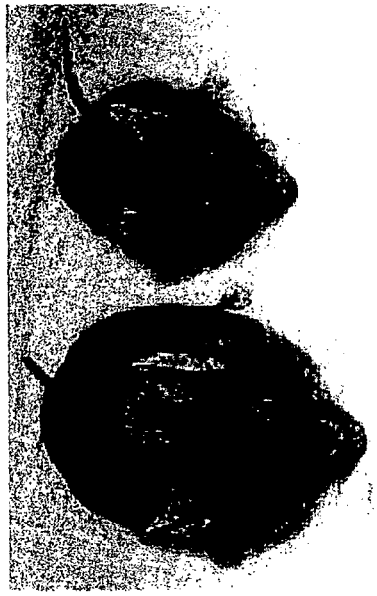
FIG. 3 shows the change of body weight of ICER Iγ Tg and WT mice.
Figure 3:
Figure 3:
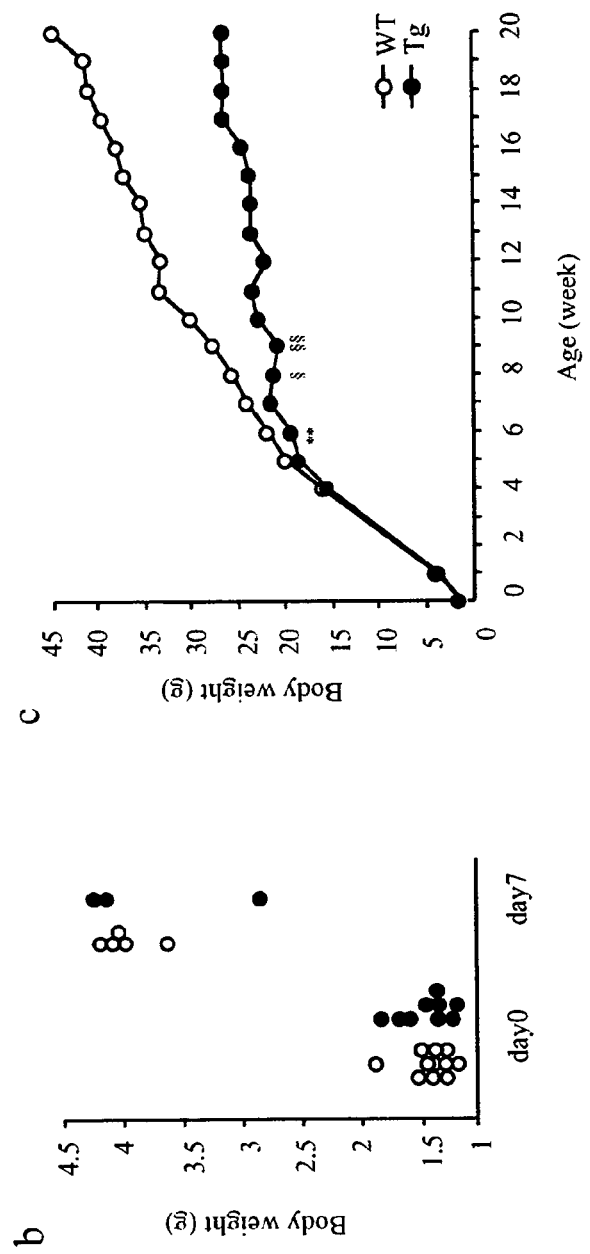

The body weights of ICER Iγ Tg mice were similar to those of the control on day 0 and day 7, but the body weights of ICER Iγ Tg mice were not increased, and slightly increased after 8 weeks of age (see FIGS. 3a and 3c).

Then, the plasma parameters and the body weights were compared in males and females of three transgenic lines, and the results are shown in Table 1.

TABLE 1

| Line | ♂♀ | Copy Number | Body weight (g) ♂ | Body weight (g) ♀ | Body glucose (mg/ml) ♂ | Body glucose (mg/ml) ♀ | Plasma insulin (pg/ml) ♂ | Plasma insulin (pg/ml) ♀ |
|---|---|---|---|---|---|---|---|---|
| Control | ♂ | 0 | 33.2 ± 0.9 | 21.7 ± 0.7 | 153 ± 4.1 | 126 ± 9.9 | 1350.3 ± 194.5 | 1480.7 ± 194.5 |
| Tg7 | ♂ | 4 | 25.8 ± 1.7$^a$ | 21.8 ± 0.6 | 527 ± 52.8$^a$ | 355 ± 61.7$^b$ | 350.5 ± 80.0$^a$ | 422.4 ± 130$^a$ |
| Tg12 | ♂ | 4 | 22.7 ± 2.6$^a$ | 22.5 ± 0.9 | 528 ± 62.1$^a$ | 336 ± 93.2$^b$ | 545.6 ± 183.7$^b$ | 654.6 ± 84.2$^b$ |
| Tg23 | ♂ | 6 | 21.7 ± 2.4$^a$ | 22.6 ± 1.0 | 551 ± 31.1$^a$ | 420 ± 59.5$^b$ | 278.1 ± 111.2$^a$ | 445.5 ± 39.7$^a$ |

$^a$P < 0.05;
$^b$P < 0.001 vs control.

Three lines (Tg7, Tg12 and Tg23) of ICER Iγ Tg mice with transgene positive were established. The results are represented by mean ±SE of at least 10 animals in each group. In either males or females at 12 weeks of age, only ICER Iγ Tg mice exhibited low insulin and hyperglycemia. The mice from Tg7 and Tg12 contain a different copy number of the transgene from that of Tg23 mice, but no significant difference was observed in body weights, blood glucose levels, and insulin levels among the three lines. These results suggest that the specific expression of ICER Iγ at a high level is strongly linked to the symptoms of severe diabetes.

Effects on Kidney

Figure 4:
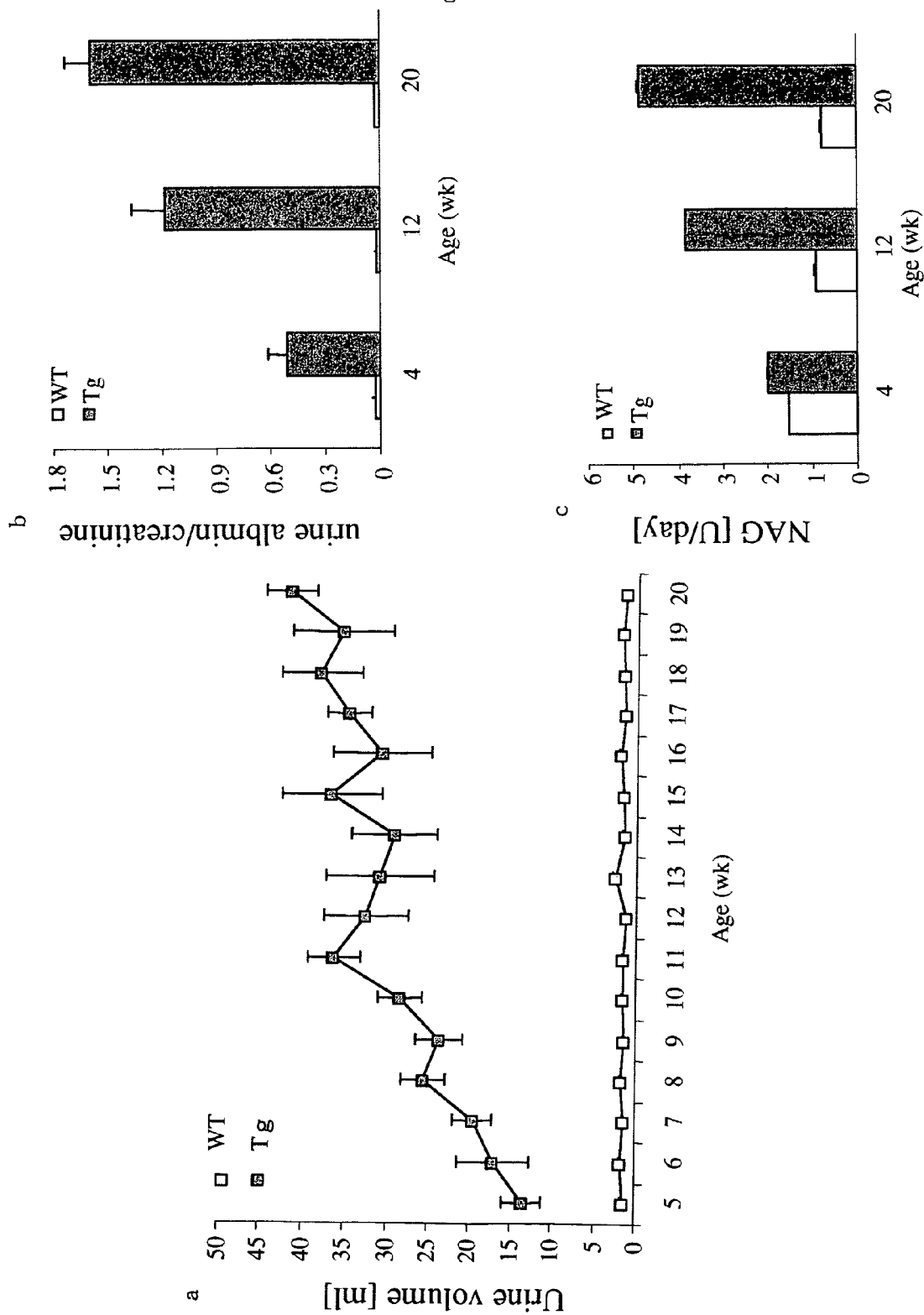
FIG. 4a shows the changes of urinary volumes, and ICER Iγ Tg mice exhibited polyuria.
FIG. 4b shows the changes of urinary albumin excretion. Proteinuria was increased in ICER Iγ Tg mice with aging.
FIG. 4c shows the changes of urinary NAG which is an indicator of renal tubular disorder. All levels of the urinary volume, urinary albumin and urinary NAG were increased with aging in ICER Iγ Tg mice. All levels of the urinary volume, urinary albumin and urinary NAG were further increased in ICER Iγ Tg mice compared with WT mice.

Furthermore, the effects on the kidney in ICER Iγ Tg mice were evaluated. Urinary volumes were examined, and polyurea was detected in ICER Iγ Tg mice (FIG. 4a). Excretion of albumin in urine was examined, and high levels of proteinuria, which increased with age, was detected in ICER Iγ Tg mice (FIG. 4b). Urinary NAG, which was a marker of renal tubular disorder, also increased with age in ICER Iγ Tg mice (FIG. 4c). Thus, urinary volume, urinary albumin and urinary NAG exhibited much higher values in ICER Iγ Tg than WT (control) mice.

Furthermore, WT and ICER Iγ Tg at 28 weeks of age were compared and analyzed. These results are shown in Table 2.

TABLE 2

| 28 wk | WT | Tg |
|---|---|---|
| Weight (g) | 33.7 ± 1.48 | 25.2 ± 1.44* |
| Blood glucose (mg/dl) | 140.3 ± 21.36 | 567.3 ± 25.54* |
| HbA1c (%) | 4.0 ± 0.15 | 12.53 ± 0.77* |
| Blood Pressure (mmHg) | 97.2 ± 1.59 | 114 ± 1.26* |
| Serum creatinine (mg/dl) | 0.37 ± 0.007 | 0.39 ± 0.003 |
| Kidney/body weight (%) | 0.73 ± 0.04 | 1.69 ± 0.26* |

In Table 2, * indicates significance at P < 0.05.

The amount of glycohemoglobin (HbA1c) was remarkably increased in ICER Iγ Tg mice as compared with WT mice. Blood pressure was lower in ICER Iγ Tg mice than in WT mice. Although the body weights of ICER Iγ Tg mice were lower than those of WT mice, a weight ratio of kidney/body weight (%) was considerably larger in ICER Iγ Tg mice than in WT mice.

Figure 5:
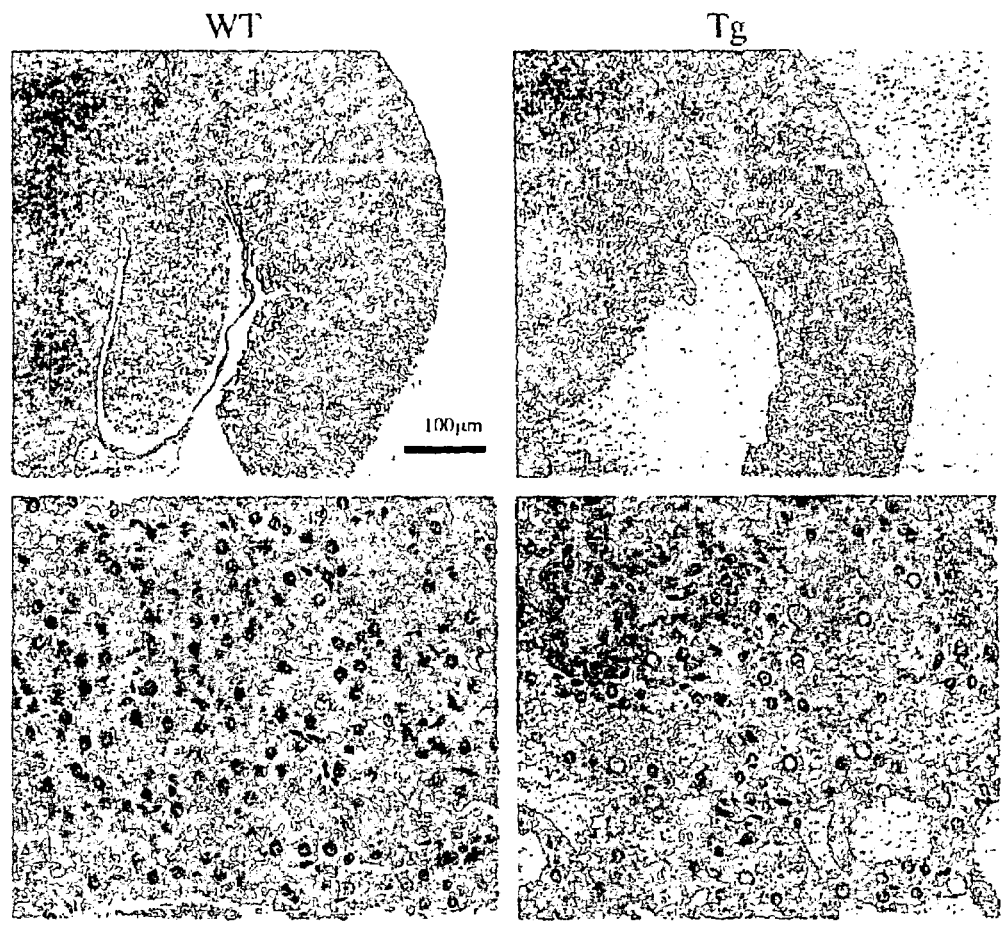
FIG. 5 shows the results obtained by giving HE staining to kidney specimens and observing by an optical microscopy. Enlargement of renal pelvis and renal tubule was observed in the Tg mice.
Figure 6:
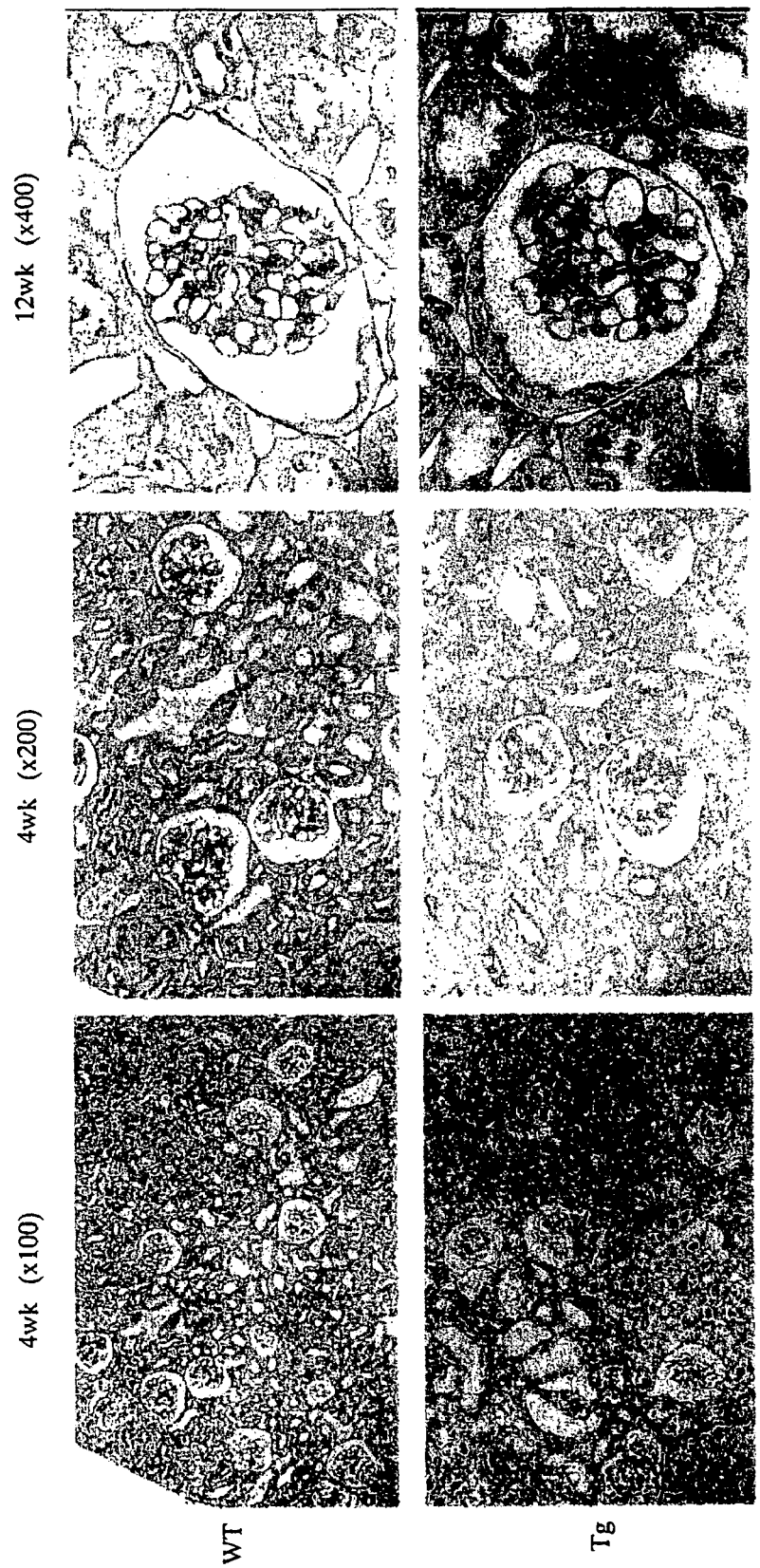
FIG. 6 shows the results obtained by giving PAS staining to kidney specimens and observing by an optical microscopy. Compared with the WT mice, glomerular hypertrophy was observed in the Tg mice at 4 weeks of age and sclerosis thereof was observed at 12 weeks.
Figure 7:
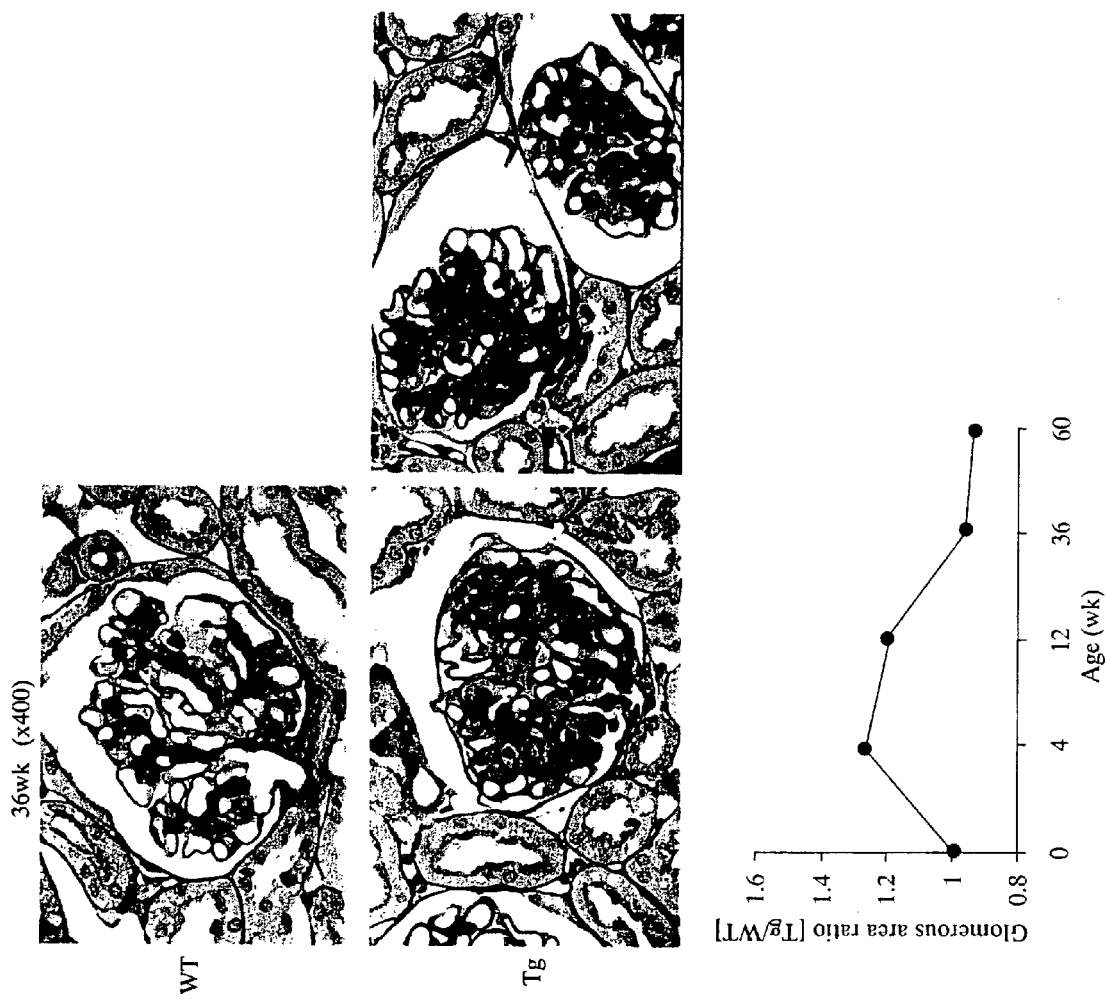
FIG. 7 shows glomerulus in the mouse at 36 weeks of age. Obvious glomerular sclerosis was observed in ICER Iγ Tg mice (FIG. 7a, b, c). The glomerular hypertrophy was quantitatively examined, and consequently the hypertrophy was observed from 4 to 12 weeks of age (FIG. 7d).
Figure 8:
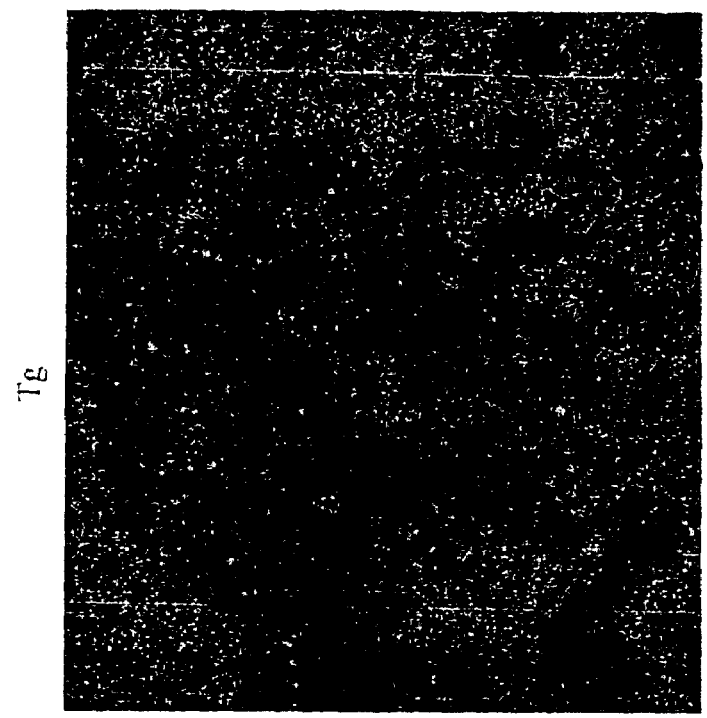
FIG. 8 shows immunohistochemical staining for collagen type IV. The increase of collagen type IV was observed in ICER Iγ Tg mice.
Figure 8:
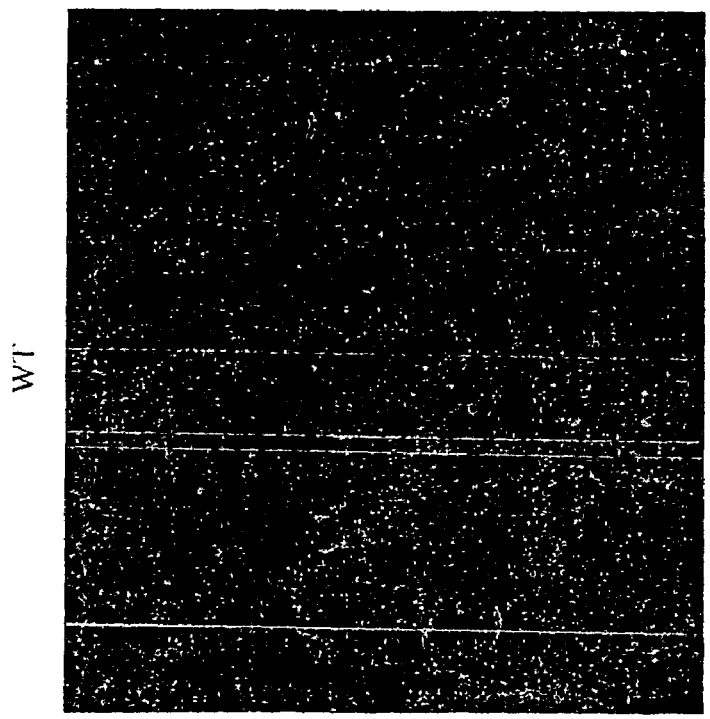
Figure 9:
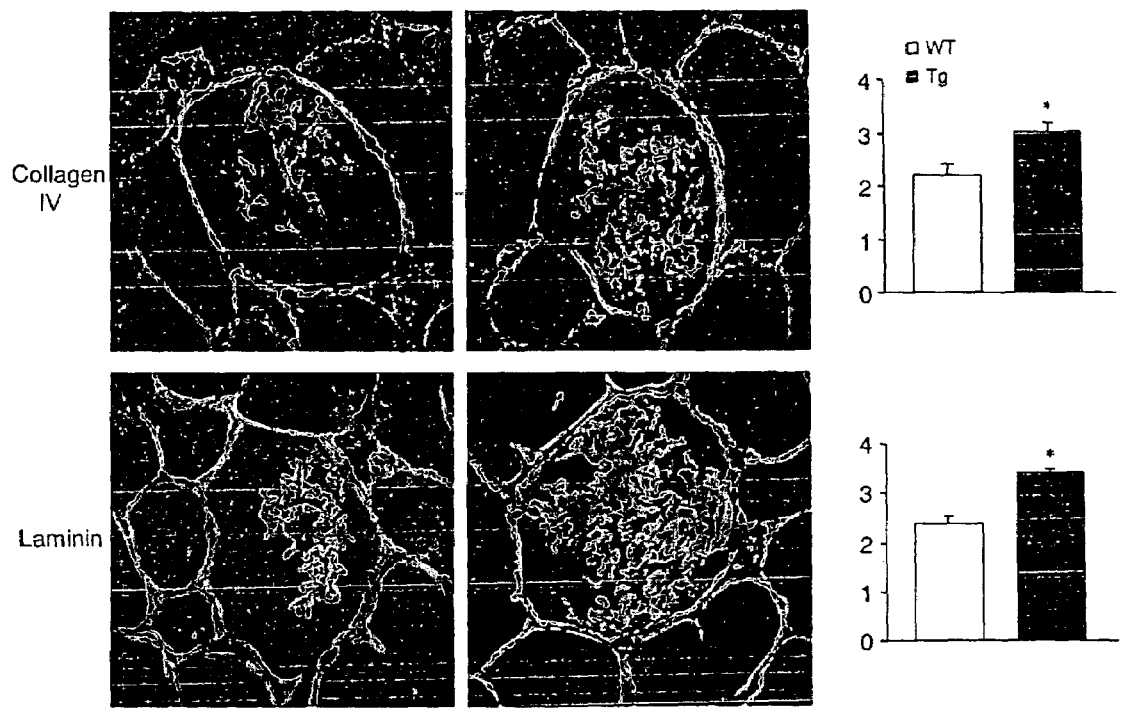
FIG. 9 shows the expression of the extracellular matrix in glomeruli by immunohistochemical staining for collagen type IV or laminin. In both of A and B, a left and a right indicate renal sections at 40 weeks of age in the WT and ICER Iγ Tg mice, respectively. C and D indicate scores obtained by determining from the renal sections. In ICER Iγ Tg mice, collagen type IV and laminin were quantitatively increased.
Figure 10:
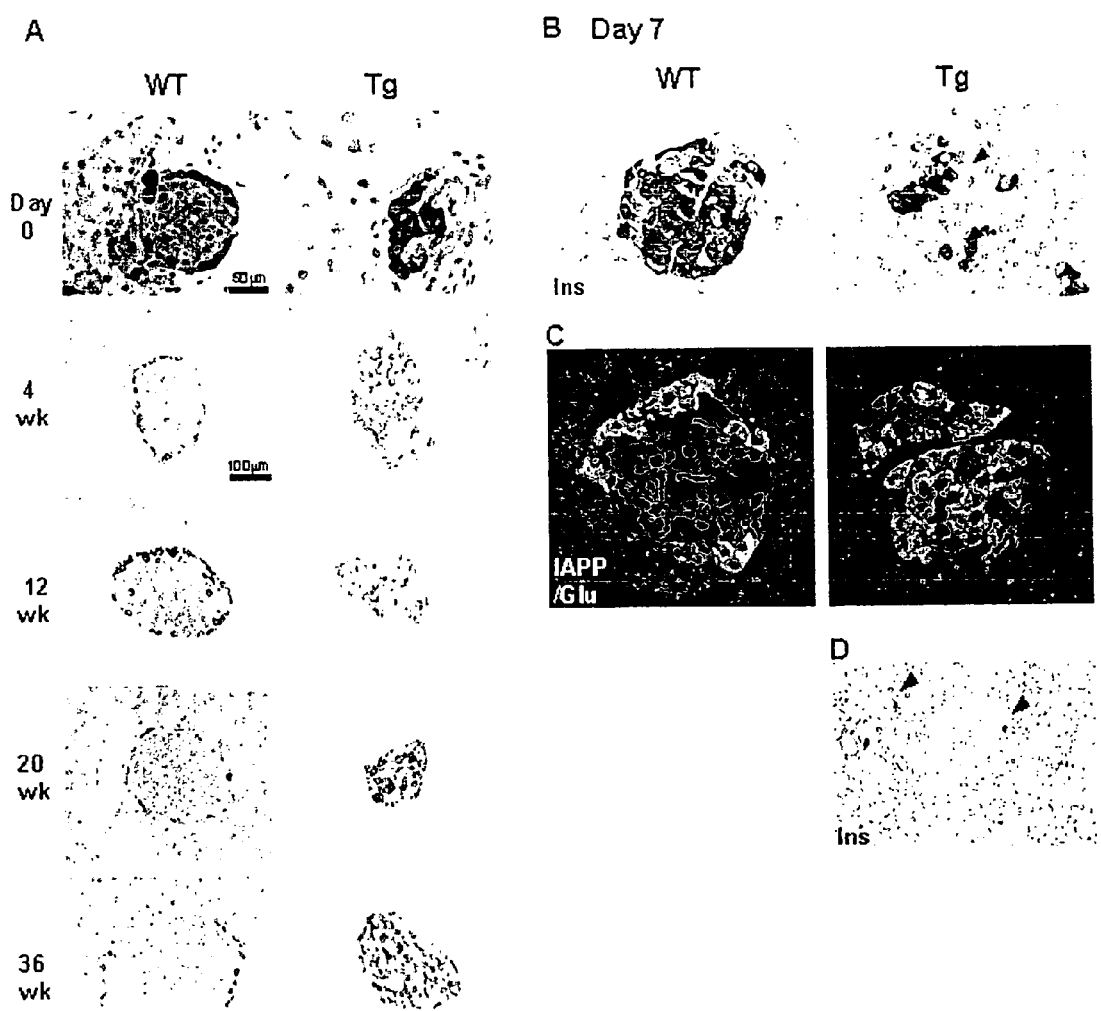
FIG. 10 shows islet morphology in mice from line Tg23.
A: Pancreatic sections from day 0 to 36 weeks of age were immunohistochemically stained using anti-insulin antibody (pink) and anti-glucagon antibody (red). In ICER Iγ Tg mice, it seems that insulin-producing cells (β cells) have been already decreased at birth (day 0) and tissue of the islets is severely disorganized with significantly increased glucagon-producing cells (glucagon +). Since the β cells were sharply decreased at day 0 at which the blood glucose level is normal, indicating that these changes result directly from the increased ICER Iγ and are not due secondarily to hyperglycemia. B: Reduced insulin-producing cells (arrow) in ICER Iγ Tg mice at 7 day after birth (×1000). In ICER Iγ Tg mice, there is a marked variation in the amount of insulin per cell (degranulation) as shown by the insulin staining.

Furthermore, the kidneys of ICER Iγ Tg mice were histologically examined. As a result, swelling of kidney and enlargement of renal pelvis and tubules were observed (FIG. 5). In ICER Iγ Tg mice, the hypertrophy of glomerulus was observed at 4 weeks of age (FIG. 6), and sclerosis thereof was observed at 12 weeks of age. Obvious glomerular sclerosis was observed in ICER Iγ Tg mice at 36 weeks of age (FIGS. 7a, 7b and 7c). The glomerular hypertrophy was quantitatively examined, and the hypertrophy was observed from 4 to 12 weeks of age (FIG. 7d). Also collagen type IV and laminin, which indicate fibrosing, were increased (FIGS. 8 and 9).

These are similar symptoms to those of human diabetic nephropathy, and indicate that the present invention is useful as the first diabetic nephropathy model mouse of the strain C57BL/6 which normally does not develop nephropathy.

By utilizing the gene or the protein of the invention, it is possible to effectively diagnose or treat nephropathy, particularly diabetic nephropathy. For example, by the use of the probe based on the gene of the invention or the antibody which binds to the protein of the invention, it is possible to diagnose or determine the onset of or elucidate the onset mechanism of nephropathy or diabetic nephropathy.

The transgenic non-human mammalian animal of the invention can be effectively utilized as a proper evaluative model of nephropathy, particularly diabetic nephropathy, because it develops the symptoms similar to nephropathy, particularly diabetic nephropathy, in humans.

Furthermore, by the use of the transgenic non-human mammalian animal of the invention, it is possible to efficiently perform the determination or diagnosis of nephropathy or diabetic nephropathy, or the screening the active component of the preventive or therapeutic agent of nephropathy or diabetic nephropathy.

The present invention provides exceptionally excellent procedures in the diagnosis or the treatment of nephropathy or diabetic nephropathy.

The invention claimed:

1. A transgenic mouse comprising either 4 or 6 copies of transgenes encoding inducible cAMP early repressor Iγ (ICER Iγ) operably linked to a human insulin promoter; wherein the transgenic mouse develops nephropathy.

2. The transgenic mouse according to claim 1, wherein the nephropathy is diabetic nephropathy.

3. The transgenic mouse according to claim 1, wherein the copy number of said transgene is 6.

4. A method for screening a therapeutic substance for at least one condition selected from the group consisting of nephropathy, diabetic nephropathy and diabetes, comprising a step of administering a subject substance to the transgenic mouse according to claim 1 and measuring an effect of the subject substance on the at least one condition selected from the group consisting of nephropathy, diabetic nephropathy and diabetes of the mouse.

* * * * *